United States Patent [19]

Perron et al.

[11] Patent Number: 5,925,555
[45] Date of Patent: *Jul. 20, 1999

[54] PROCESS FOR THE PRODUCTION OF A VIABLE CELL CULTURE INFECTED BY A MULTIPLE SCLEROSIS-ASSOCIATED VIRUS

[75] Inventors: Herve Perron, Grenoble; Jean-Marie Seigneurin, Bernin, both of France

[73] Assignees: Bio Merieux, L'Etoile; Universite Joseph Fourier (Grenoble 1), Grenoble Cedex, both of France

[ * ] Notice: This patent is subject to a terminal disclaimer.

[21] Appl. No.: 08/651,573

[22] Filed: May 22, 1996

Related U.S. Application Data

[62] Division of application No. 08/157,060, Feb. 2, 1994, Pat. No. 5,585,262, which is a division of application No. PCT/FR93/00337, Apr. 2, 1993.

[30] Foreign Application Priority Data

| Apr. 3, 1992 | [FR] | France | 92 04322 |
| Nov. 3, 1992 | [FR] | France | 92 13447 |

[51] Int. Cl.$^6$ ..................... C12N 5/00
[52] U.S. Cl. ............ 435/235.1; 435/239; 435/325
[58] Field of Search ............ 435/235.1, 240.2, 435/325

[56] References Cited

U.S. PATENT DOCUMENTS

| 4,311,686 | 1/1982 | Angers et al. |
| 4,346,074 | 8/1982 | Gilmour et al. |
| 4,388,298 | 6/1983 | Nazerian et al. |
| 4,396,600 | 8/1983 | Messineo et al. |
| 4,520,113 | 5/1985 | Gallo et al. |
| 4,647,773 | 3/1987 | Gallo et al. |
| 4,708,818 | 11/1987 | Montagnier et al. |
| 4,900,553 | 2/1990 | Silver et al. |
| 5,158,976 | 10/1992 | Rosenberg et al. |
| 5,219,837 | 6/1993 | Cohen et al. |
| 5,225,352 | 7/1993 | Zanetta et al. |
| 5,585,262 | 12/1996 | Perron et al. |

FOREIGN PATENT DOCUMENTS

| 0 222 310 | 5/1987 | European Pat. Off. |
| 0 326 395 | 8/1989 | European Pat. Off. |
| 93/07259 | 4/1993 | WIPO |
| 93/20188 | 10/1993 | WIPO |
| WP 93/23550 | 11/1993 | WIPO |
| WO 94/28138 | 12/1994 | WIPO |

OTHER PUBLICATIONS

R. Lisak et al., "In Vitro Cell–Mediated Immunity of Cerebrospinal–Fluid Lymphocytes To Myelin Basic Protein In Primary Demyelinating Diseases", *The New England Journal of Medicine*, vol. 297, No. 16, Oct. 20, 1977, pp. 850–853.

C.R. Bangham et al., "PCR Analysis of DNA from Multiple Sclerosis Patients for the Presence of HTLV–I", *Science*, vol. 246, Nov. 10, 1989, pp. 821–824.

E. J. Field, "Immunological Treatment for Multiple Sclerosis", *The Lancet*, Jun. 3, 1989, p. 1272.

D. Johnson et al., "Quantitation of the Myelin–Associated Glycoprotein in Human Nervous Tissue from Controls and Multiple Sclerosis Patients", *Journal of Neurochemistry*, vol. 46, No. 4, 1986, pp. 1086–1093.

R. T. Johnson, "Nononcogenic Retrovirus Infections as Models for Chronic and Relapsing Human Diseases: Introduction", *Reviews of Infectious Diseases*, vol. 7, No. 1, Jan.–Feb. 1985, pp. 66–67.

S. L. Hauser et al., "Analysis of Human T–lymphotropic Virus Sequences in Multiple Sclerosis Tissue", *Nature*, vol. 322, Jul. 10, 1986, pp. 176–178.

H. Lassmann et al., "Chronic Relapsing Experimental Allergic Encephalomyelitis—Clinicopathological Comparison With Multiple Sclerosis", *Arch Neurol*, vol. 36, Aug. 1979, pp. 490–497.

A. T. Haase, "Pathogenesis of Lentivirus Infections", *Nature*, vol. 322, Jul. 10, 1986, pp. 130–136.

N. Nathanson et al, "Experimental Visna in Icelandic Sheep: The Prototype Lentiviral Infection", *Reviews of Infectious Diseases*, vol. 7, No. 1, Jan.–Feb. 1985, pp. 75–82.

S. Haahr et al., "Just Another Dubious Virus in Cells from a Patient with Multiple Sclerosis?", *The Lancet*, vol. 337, Apr. 6, 1991, pp. 863–864.

M. Ohta et al., "Sera from Patients with Multiple Sclerosis React with Human T Cell Lymphotropic Virus–I Gag Proteins But Not Env Proteins—Western Blotting Analysis", *The Journal of Immunology*, vol. 137, No. 11, Dec. 1, 1986, pp. 3440–3443.

H. Korpowski et al., "Multiple Sclerosis and Human T–cell Lymphotropic Retrovirusus", *Nature*, vol. 318, Nov. 14, 1985, pp. 154–160.

S. J. Greenberg et al., "Detection of Sequences Homologous to Human Retroviral DNA in Multiple Sclerosis by Gene Amplification", *Proc. Natl. Acad. Sci. USA*, vol. 86, Apr. 1989, pp. 2878–2882.

E. P. Reddy et al., "Amplification and Molecular Cloning of HTLV–I Sequences from DNA of Multiple Sclerosis Patients", *Science*, vol. 243, Jan. 27, 1989, pp. 529–533.

(List continued on next page.)

*Primary Examiner*—Leon B. Lankford, Jr.
*Attorney, Agent, or Firm*—Oliff & Berridge, PLC

[57] ABSTRACT

The present invention relates to a process for in vitro culture of cells infected by a virus associated with multiple sclerosis and to the infected cell lines thus produced. According to the invention, the process includes: a) cultivation of human cells infected by a viral strain to obtain at least one culture of primary cells infected by the viral strain, b) cultivation of non-infected human cells permissive to the viral strain to obtain at least one permissive culture, c) cocultivation of at least one sample of a culture of infected primary cells and one sample of the permissive culture to obtain a first infected derived culture, d) cultivation in series of the first infected derived culture. The invention is used in particular in the pharmaceutical diagnostics industry sector.

16 Claims, 1 Drawing Sheet

OTHER PUBLICATIONS

K. G. Warren et al., "Diagnostic Value of Cerebrospinal Fluid Anti–Myelin Basic Protein in Patients with Multiple Sclerosis", *Annals of Neurology,* vol. 20, No. 1, Jul. 1986, pp. 20–25.

O. Narayan et al., "Lentiviral Diseases of Sheep and Goats: Chronic Pneumonia Leukoencephalomyelitis, and Arthritis", *Reviews of Infectious Diseases,* vol. 7, No. 1, Jan.–Feb. 1985, pp. 89–98.

A. Gessain et al., "Intrathecal Synthesis of Antibodies to Human T Lymphotrophic Virus Type I and the Presence of IgG Oligoclonal Bands in the Cerebrospinal Fluid of Patients with Endemic Tropical Spastic Paraparesis", *The Journal of Infectious Diseases,* vol. 157, No. 6, Jun. 1988, pp. 1226–1234.

*ATCC Catalouge of Cell Lines and Hybridomas,* Sixth Edition, 1988, pp. 165 and 344–355.

Bjare, "Serum–Free Cell Culture", *Pharmac. Ther.,* vol. 53, 1992, pp. 355–374.

H. Perron et al., "Leptomeningeal Cell Line from Multiple Sclerosis with Reverse Transcriptase Activity and Viral Particles", *Biological Abstracts,* vol. 89, No. 9, May 1, 1990.

H. Perron et al., "Isolation of Retrovirus from Patients with Multiple Sclerosis", *The Lancet,* vol. 337, No. 8745, Apr. 6, 1991, pp. 862–863.

C. Bosgiraud et al., "Ultrastructural Study on Visna Virus in Sheep Plexus Choroid Cells", *Biological Abstracts,* vol. 83, No. 7, 1987.

Acha–Orbea et al., "Mls—A Retrovirus Exploits the Immune System", *Immunology Today,* vol. 12, No. 10, 1991, pp. 356–361.

Asai et al., "J. of Neurochem", vol. 59, No. 1, pp. 307–317, 1992.

R. Baccala et al., "Genomically Imposed and Somatically Modified Human Thymocyte vb Gene Repertoires", *Proc. Natl. Acad. Sci.,* vol. 88, pp. 2908, 1991.

Barna et al., "Human Astrocytes Proliferate in Response to Tumor Necrosis Factor Alpha", *J. Neuroimmunol.,* 30 (1990), pp. 239–243.

Beck et al., "Increased Production of Interferon Gamma and Tumor Necrosis Factor Precedes Clinical Manifestation in Multiple Sclerosis: Do Cytokines Trigger Off Exacerbations?", *Acta Neurol. Scand.,* 1988: 78, pp. 318–323.

Bergamini et al., "Multiple Sclerosis. I. The Immune Pathogenetic Hypothesis", *Riv. Neurol.,* vol. 59, No. 5, Oct. 1989, pp. 176–190.

T. Bergström et al., "Isolation of Herpes Virus Type 1 During First Attack of Multiple Sclerosis.", *Annales Neurology,* vol. 26, pp. 283–285, (1989).

Bernton et al., "No Direct Neuronotoxicity by HIV–1 Virions or Culture Fluids from HIV–1 Infected T Cells or Monocytes", *Aids Research and Human Retroviruses,* vol. 8, No. 4, 1992, pp. 495–503.

Birnbaum et al., "Spinal Fluid Lymphocytes from a Sub-Group of Multiple Sclerosis Patients Respond to Mycobacterial Antigens", *Ann. Neurol.,* vol. 34, No. 1, Jul. 1993, pp. 18–24.

D. Ross Boswell et al., "Sequence comparison and alignment: the measurement and interpretation of sequence similarity", *Computational Molecular Biology, Sources and Methods for Sequence Analysis,* pp. 161–178.

Boyle et al., "Cellular Immune Response in Multiple Sclerosis Plaques", *American Journal of Pathology,* vol. 137, No. 3, Sep. 1990, pp. 575–584.

Bradford, A Rapid and Sensitive Method for the Quantitation of Microgram Quantities of Protein Utilizing the Principle of Protein–Dye Binding, *Anal. Biochem.,* 72, 1976, pp. 248–254.

Brocke et al., "Induction of Relapsing Paralysis in Experimental Autoimmune Encephalomyelitis by Bacterial Superantigen", *Nature,* vol. 365, Oct. 14, 1993, pp. 642–644.

Calder, et al., "MS: A Localized Immune Disease of the Central Nervous System", *Immunology Today,* vol. 10, No. 3, 1989, pp. 99–103.

Carp et al."Viral Etiology of Multiple Sclerosis", *Prog. Med. Virol.,* vol. 24, pp. 158–177, 1978.

Charcot, "Histologie de la sclerose en plaques [Histology of Multiple Sclerosis]", Gaz. Hop. (Paris), 1868; 41, 554–66.

Chomczynski et al., "Single–Step Method of RNA Isolation by Acid Guanidinium Thiocyanate–Phenol–Chloroform Extraction", *Anal. Biochem.,* 1987, vol. 162, pp. 156–159.

Cole et al., "The Mycoplasma Arthritidis T–Cell Mitogen, MAM: A Model Superantigen", *Immunology Today,* vol. 12, No. 8, 1991, pp. 271–276.

Cook et al., "Multiple Sclerosis and Distemper in Iceland 1966–1978", *Acta Neurol. Scandinav.* 61, 1980, pp. 244–251.

Dalgleish et al., "Do Human T–Lymphotrophic Viruses (HTLVs) and Other Enveloped Viruses Induce Autoimmunity in Multiple Sclerosis?", *Neuropath. App. Neurobiol.,* 1987, 13, pp. 241–250.

A. N. Davison et al., "Biosynthesis of Myelin and Neurotoxic Factors in the Serum of Multiple Sclerosis Patients", *Advances in Experimental Medicine and Biology,* vol. 100, pp. 19–25, 1978.

De Keyser, "Autoimmunity in Multiple Sclerosis", *Neurology,* 38, Mar. 1988, pp. 371–374.

S. Dhib–Jalbut et al., "Measles Virus Polypeptide–Specific Antibody Profile in Multiple Sclerosis", *Neurology,* vol. 40, pp. 430–435, (1990).

Dunn et al., "A Novel Method to Map Transcripts: Evidence for Homology Between an Adenovirus mRNA and Discrete Multiple Regions of the Viral Genome", *Cell,* vol. 12, Sep. 1977, pp. 23–36.

Ebers et al., "The Geography of MS Reflects Genetic Susceptibility", *Neurology,* 36, Apr. 1986, Suppl. 1, p. 108.

Elian et al., "Multiple Sclerosis Among United Kingdom–Born Children of Immigrants from the Indian Subcontinent, Africa and the West Indies", *J Neurol Neurosurg Psychiat,* 1990; 53, pp. 906–911.

Escourolle et al., "Principales Donnees Morphologiques Approches Physiopathologiques et Etiologiques de la Sclerose en Plaques [Principal Morphological Data, Physiopathological and Etiological Approaches to Multiple Sclerosis]", *La Reveue du Praticien,* Paris, 1980; 30, pp. 2047–2053.

Frohman et al., "Rapid Production of Full Length cDNAs from Rare Transcripts: Amplification Using a Single Gene–Specific Oligonucleotide Primer", *Proc. Natl. Acad. Sci. USA,* 1988, vol. 85, pp. 8998–9002.

Medline Abstract of FU et al., "Rabies virus nucleoprotein expressed in and purified from insect cells is efficacious as a vaccine," Proc Natl Acad Sci USA 88: 2001–05 (1991).

Galiana et al., "Establishment of Permanent Astroglial Cell Lines, Able to Differentiate in Vitro, From Transgenic Mice Carrying the Polyoma Virus Large T Gene: An Alternative Approach to Brain Cell Immortalization", *Journal of Neuroscience Research,* 1990; 26: pp. 269–277.

M. B. Gardner et al., "Congenital Transmission of Murine Leukaemia Virus from Wild Mice Prone to Development of Lymphoma and Paralysis", *J. Natl. Cancer Inst.*, vol. 62, pp. 63–69, (1979).

M. B. Gardner, Genetic resistance to a Retroviral Neurologic Disease in Wild Mice, in "Retrovirus Infections of the Nervous System", *Oldstone M.B.A. and Koprowsky H. Eds. Current Topice in Microbiology and Immunology*, No. 160, pp. 3–10, (Springer–Verlag, Berlin, 1990).

Gay, "Is Multiple Sclerosis Caused by an Oral Spirochaete", *The Lancet*, Jul. 12, 1986, pp. 75–77.

A. Gessain et al., Antibodies to Human T–Lymphotrophic Virus type–I in Patients with Tropical Spastic Paraparesis, *Lancet*, vol. 2, pp. 407–410, (1985).

Giulian et al., "The Envelope Glycoprotein of Human Immunodeficiency Virus Type 1 Stimulates Release of Neurotoxins from Monocytes", *Proc. Natl. Acad. Sci. USA*, vol. 90, 1993, pp. 2769–2773.

D. Giulian et al., "Secretion of Neurotoxins by Mononuclear Phagocytes Infected with HIV–1", *Science*, vol. 250, Dec. 14, 1990, pp. 1593–1596.

Gonzalez–Scarano et al., "Multiple Sclerosis Disease Activity Correlates with Gadolinium–Enhanced Magnetic Resonance Imaging", *Annals of Neurology*, vol. 21, No. 3, Mar. 1987, pp. 300–306.

F. Gonzalez–Scarano et al., "Sequence Similarities Between Human Immunodeficiency Virus gp41 and Paramyxovirus Fusion Proteins.",*AIDS Res. Hum. Retrov.*, vol. 3, pp. 245–252, (1987).

S. Haahr et al., "A Putative New Retrovirus Associated with Multiple Sclerosis and the Possible Involvement of Epstein-–Barr Virus in this Disease", *NY Acad. Science*, vol. 724, pp. 148–156, 1994.

S. Haahr et al., "Is Multiple Sclerosis Caused by a Dual Infection with Retrovirus and Epstein–Barr Virus?", *Neuroepidemiology*, vol. 11, pp. 299–303, (1992).

Haegert et al. HLA–DRβ, –DQα, and DQβ Restriction Fragment Length Polymorphisms in Multiple Sclerosis, *J. Neurosci. Res.*, 1989; 23, pp. 46–54.

Hauw et al., "Aspects Anatomo–Pathologiques de la Sclerose en Plaques [Anatomopathological Aspects of Multiple Sclerosis]", *La Sclerose en Plaques [Multiple Sclerosis]*, 9–47 (Rascol et al. eds., 1980).

Hirayama et al., "Serum–Mediated Oligodendrocyte Cytotoxicity in Multiple Sclerosis Patients and Controls", *Neurology* 1986, vol. 36, pp. 276–278.

Hoffman et al., "Handbook of Clinical Neurology, 12; Viral Diseases", R.R. McKendall, ed., Elsevier Science Publishing, Amsterdam, 1989, pp. 453–466.

Huang, "Defective Interfering Viruses", *Fundamental Virology*, Fields et al., eds., 1986, pp. 101–117.

Huck et al., "J. of Neurosei", vol. 4, No. 10, pp. 2650–2657, 1984.

A.W. Hugin et al., "A Virus–Encoded Superantigen in a Retrovirus–Induced Immunodeficiency Syndrome of Mice", *Science*, vol. 252, pp. 424–427, (1991).

James, "Multiple Sclerosis or Blood–Brain Barrier Disease", *The Lancet*, Jan. 7, 1989, p. 46.

Medline abstract of Jarrett et al., "Studies on vaccination against papillomaviruses: a comparison of purified virus, tumor extract and transformed cells in prophylactic vaccination," Vet Rec 126: 449–452 (1990).

Jervis et al., "Experimental Allergic Encephalomyelitis", *J. Neuropathol. Exp. Neurol.*, 1948; 7, pp. 309–320.

D. Johnson et al., "Quantitation of the Myelin–Associated Glycoprotein in Human Nervous Tissue from Controls and Multiple Sclerosis Patients", *Journal of Neurochemistry*, vol. 46, No. 4, 1986, pp. 1086–1093.

Johnson, "Viral Aspects of Multiple Sclerosis", *Handbook of Clinical Neurology*, vol. 3(47): Demyelinating Diseases, 1985, pp. 319–336.

Juntunen et al. "Multiple Sclerosis and Occupational Exposure to Chemicals: A Co–Twin Study of a Nationwide Series of Twins", *Br. J. Int. Med.*, 1989; 46: pp. 417–419.

Karpas et al., "Lack of evidence for involvement of known human retroviruses in multiple sclerosis", *Nature*, vol. 322, Jul. 10, 1986, pp. 177–178.

Kent et al., "Cerebral Blood Flow, Cerebral Metabolism and Blood–Brain Barrier," *Handbook of Clinical Neurology*, vol. 56(12), 1989, pp. 79–91.

G. La Mantia et al., "Identification of New Human Repetitive Sequences: Characterization of the Corresponding cDNAs and their Expression in Embryonal Carcinoma Cells", *Nucleic Acids Research*, vol. 17, No. 15, 5913–5922, (1989).

G. La Mantia et al., "Identification and Characterization of Novel Human Endogenous Retroviral Sequences Prefentially Expressed in Undifferentiated Embryonal Carcinoma Cells", *Nucleic Acids Res.*, 1991, vol. 19, No. 7, pp. 1513–1520.

Medline abstract of LEAO, "Tuberculosis: new strategies for the development of diagnostic tests and vaccines," Braz J Med Biol Res 26: 827–833 (1993).

Levi et al., Human Immunodeficiency Coat Protein gp120 Inhibits the β–adrenergic Regulation of Astroglial and Microglial Functions, *Proc. Natl. Acad. Sci. USA*, vol. 90, Feb. 1993, pp. 1541–1545.

Levine et al., "Conversion of Lytic to Persistent Alphavirus Infection by the bcl–2 Cellular Oncogene", *Nature*, vol. 361, Feb. 25, 1993, pp. 739–742.

Y.S. Lie et al., Journal of Virology, vol. 68, No. 12, Dec. 1994, pp. 7840–7849, "Chinese hamster ovary cells contain transcriptionally active full length type C proviruses".

Linial et al., "Retroviral RNA Packaging: Sequence Requirements and Implications", in *Current Topics in Microbiology and Immunobiology. Retroviruses, Strategies of Replication*, Swanstrom et al., eds., vol. 157, 1990, pp. 125–152.

Lo et al, "Newly Discovered Mycoplasma Isolated from Patients Infected with HIV", *The Lancet*, vol. 338, Dec. 7, 1991, pp. 1415–1418.

Lori et al., "Viral DNA Carried by Human Immunodeficiency Virus Type 1 Virions", *J. Virol.*, vol. 66, No. 8, Aug. 1992, pp. 5067–5074.

F. Mallet et al., "Continuous RT–PCR and taq DNA Polymerase: Characterization and Comparison to Uncoupled Procedures", Biotechniques, vol. 18, pp. 678–687, 1985.

Mallet et al., "Enzyme–Linked Oligosorbent Assay for Detection of Polymerase Chain Reaction–Amplified Human Immunodeficiency Virus Type I", *J. Clin. Microbiol.*, Jun. 1993, vol. 31, No. 6, pp. 1444–1449.

Marie, "Sclerose en Plaques et Maladies Infectieuses [Multiple Sclerosis and Infectious Diseases]", *Le Progres Medical*, 1884; 12, pp. 287–289.

P. Marrack et al., "A Maternally Inherited Superantigen Encoded by a Mammary Tumor Virus", *Nature*, vol. 349, pp. 524–526, (1991).

McDonald, "The Mystery of the Origin of Multiple Sclerosis", *J. Neurol. Neurosurg. Psych.*, 1986; 49, pp. 113–123.

J. Merregaert et al., "Nucleotide Sequence of a Radiation Leukemia Virus Genome", *Virology,* vol. 158, No. 1, pp. 88–102, (1987).

Meyerhans et al., "Temporal Fluctuations in HIV Quasispecies in Vivo Are Not Reflected by Sequential HIV Isolations", *Cell,* vol. 58, Sep. 8, 1989, pp. 901–910.

J.D. Mosca et al., "Activation of human immunodeficiency virus by herpesvirus infection: Identification of a region within the long terminal repeat that responds to a trans–acting factor encoded by herpes simplex virus 1", *Proceedings of the National Academy of Sciences of USA,* vol. 84, No. 21, Nov. 1987, pp. 7408–7412.

Mosmann, "Rapid Colorimetric Assay for Cellular Growth and Survival: Application to Proliferation and Cytotoxicity Assays", *Journal of Immunological Methods,* 65, 1983, pp. 55–63.

Newell et al., "Ligation of Major Histocompatibility Complex Class II Molecules Mediates Apoptotic Cell Death in Resting B Lymphocytes", *Proc. Natl. Acad. Sci. USA,* vol. 90, Nov. 1993, pp. 10459–10463.

Nielsen et al., "Sequence–Selective Recognition of DNA by Strand Displacement with a Thymine–Substituted Polyamide", *Science,* vol. 254, pp. 1497–1500.

Norby, "Viral Antibodies in Multiple Sclerosis", *Prog. Med. Virol.,* vol. 24 1978, pp. 1–39 (1978).

Medline abstract of Orlandi et al., "Characterization of the 175–kilodalton erythrocyte binding antigen of Plasmodium falciparum," Mol Biochem Parasitol 40: 285–294 (1990).

Ostrove et al., "Activation of the Human Innumodeficiency Virus by Herpes Simplex Virus Type 1", J Virol 61 (12), Dec. 1987, pp. 3726–3732.

J.L. Pablos et al., "A novel retroviral POL sequence is present in patients with rheumatoid arthritis", & American College of Rheumatology 57th Annual Scientific Meeting, Nov. 7–11, 1993 San Antonio, Texas, USA, *Arthritis and Rheumatism,* vol. 36, No. 9, supl. 1993, p. S55, Abstract No. 102.

Medline abstract of PEI et al., "Identification purification, and characterization of major antigenic proteins of Campylobacter jejuni," J Biol Chem 266: 16363–69 (1991).

H. Perron et al., "Isolations of an Unknown Retrovirus from CSF, Blood and Brain Cells of Patients with Multiple Sclerosis", in *Current Concepts in Multiple Sclerosis,* Wietholter et al., eds., 1991, Elsevier publ., pp. 111–116.

H. Perron et al., "Leptomeningeal cell line from multiple sclerosis with reverse transcriptase activity and viral particles", *Res. Virol.,* Nov. 1989, vol. 140(6), pp. 551–561.

H. Perron et al., "Antibody to Reverse Transcriptase of Human Retrovirus in Multiple Sclerosis", Biological Abstracts, vol. 93, No. 6, Mar. 15, 1992.

H. Perron et al., "Herpes simplex virus ICPO and ICP4 immediate early proteins strongly enhance expression of a retrovirus harboured by a leptomeningeal cell line from a patient with multiple sclerosis", The Journal of General Virology, vol. 74, No. 1, Jan. 1993, pp. 65–72.

H. Perron et al., "Retrovirus Isolation from Patients with Multiple Sclerosis: Epiphenomenon or Causative Factor?", *AIDS Research and Human Retroviruses,* vol. 8, No. 5, May 1992, p. 922.

H. Perron et al., "In Vitro Transmission and Antigenicity of a Retrovirus Isolated from Multiple Sclerosis Patient", *Res. Virol.,* vol. 143, No. 5, 1992, pp. 337–350.

Perron et al., "Retroviral Reactivation by Herpesviruses in MS: Serological Arguments", Current Concepts in Multiple Sclerosis 1991, pp. 331–332.

A. Plaza et al., Theofilopoulos, A.N. New Human vβ 12DD Genes and Polymorphic Variants. J. Imm; vol. 147, No. 12, pp. 4360–4365, 1991.

Poirier et al., "La Barriere Hemato–Encephalique. Donnees Morphologiques [The Blood–Brain Barrier. Morphological Data]", *La Revue de Medecine Interne,* vol. IV, No. 2, Jun. 1983, pp. 131–144.

J. L. Portis, "Wild Mouse Retrovirus: Pathogenesis in Retrovirus Infections of the Nervous System". Oldstone M.B.A. and Koprowsky H. Eds. Current topics in microbiology and immunology, n°160, pp. 11–27, (Springer–Verlag, Berlin, 1990).

C.M. Poser et al., New Diagnostic Criteria for Multiple Sclerosis: Guidelines for Research Protocols, in "The diagnosis of Multiple Sclerosis", *Thieme Stratton Inc.,* pp. 225–229, 1984.

D.N., Posnet, "Do Superantigens Play a Role in Autoimmunity?", *Semin. Immunol.,* vol. 5, pp. 65–72, 1993.

Prineas, "The Neuropathology of Multiple Sclerosis", *Handbook of Clinical Neurology,* vol. 3 (47), 1985, pp. 213–257.

Prineas et al., "Multiple Sclerosis: Remyelination of Nascent Lesions", *Annals of Neurology,* vol. 33, No. 2, Feb. 1993, pp. 137–151.

Prineas, "Pathology of the Early Lesion in Multiple Sclerosis", *Human Pathology,* vol. 6, No. 5, Sep. 1975, pp. 531–554.

Prineas et al., "Macrophages, Lymphocytes, and Plasma Cells in the Perivascular Compartment in Chronic Multiple Sclerosis", *Laboratory Investigation,* vol. 38, No. 4, 1978, pp. 409–421.

Ransohoff et al., "Heat–Shock Proteins and Autoimmunity: Implications for Multiple Sclerosis", *Annals of Neurology,* vol. 34 No. 1, Jul. 1993, pp. 5–7.

Rapoport, *Blood–Brain Barrier in Physiology and Medicine,* 129 (1976).

S. S. Rhee et al., "A single Amino Acid Substitution Within the Matrix Protein of a D–Type Retrovirus Converts Its Morphogenesis to that of a C–Type Retrovirus", Cell 63, pp. 77–86, (1990).

Riise et al., "Clustering of Residence of Multiple Sclerosis Patients at Age 13 to 20 Years in Hordaland, Norway", *Am J Epidemiol* 1991, vol. 133, No. 9, pp. 932–939.

Robbins et al., "Production of Cytotoxic Factor for Oligodendrocytes by Stimulated Astrocytes", *The Journal of Immunology,* vol. 139, No. 8, Oct. 15, 1987, pp. 2593–2597.

Rosati et al., "Incidence of Multiple Sclerosis in the Town of Sassari, Sardinia, 1965 to 1985: Evidence for Increasing Occurrence of the Disease", *Neurology* 38 (Mar. 1988), pp. 384–388.

Rudge, "Does a Retrovirally Encoded Superantigen Cause Multiple Sclerosis?", *J. Neurology Neurosurgery & Psychiatry* 1991, vol. 54, pp. 853–855.

Medline abstract of Rumschlag et al., "Immunologic characterization of a 35–kilodalton recombinant antigen of Mycobacterium tuberculosis," J Clin Microbiol 28: 591–95 (1990).

Medline abstract of Sakulramrung et al., "Antigenic and immunogenic characteristics of subcellular fractions and whole cells of a rough *E. coli* 0111 (J5) mutant," Immunobiology 169: 372–88 (1985).

Selmaj, et al., "Tumor Necrosis Factor Mediates Myelin and Oligodendrocyte Damage In Vitro", *Annals of Neurology,* vol. 23, No. 4, Apr. 1988, pp. 339–346.

Shih et al., "Detection of Multiple, Novel Reverse Transcriptase Coding Sequences in Human Nucleic Acids: Relation to Primate Retroviruses", *J. Virol.* Jan. 1989, vol. 63, No. 1, pp. 64–75.

Silberberg et al., "Tissue Culture Demyelination by Normal Human Seurm", *Annals of Neurology*, vol. 15, No. 6, Jun. 1994, pp. 575–580.

M. Sommerlund et al., "Retrovirus–like particles in and Epstein–Barr virus–producing cell line derived from a patient with chronic progressive myelopathy", *Acta Neurol Scand*, 1993: 87: pp. 71–76.

P. Sonigo et al., "Nucleotide Sequence of Mason–Pfizer Monkey Virus: An immunosuppressive D–Type Retrovirus", Cell 45, pp. 375–385, (1986).

Southern, "Detection of Specific Sequences Among DNA Fragments Separated by Gel Electrophoresis", *J. Mol. Biol.*, 1975, vol. 98, pp. 503–517.

Suzumura et al., "Serum Cytotoxicity to Oligodendrocytes in Multiple Sclerosis and Controls: Assessment by $^{51}$Cr Release Assay", *J. Neuroimmunol.*, 11 (1986), pp. 137–147.

Traugott, "Multiple Sclerosis: Relevance of Class I and Class II MHC–Expressing Cells to Lesion Development", *Journal of Neuroimmunology*, 16, 1987, pp. 283–302.

Waksman, "Mechanisms in Multiple Sclerosis", *Nature*, vol. 318, Nov. 14, 1985, pp. 104–105.

Williams et al., "Molecular Regulation of Apoptosis: Genetic Controls on Cell Death", *Cell*, vol. 74, Sep. 10, 1993, pp. 777–779.

Wienfield et al., "Stress Proteins Autoimmunity, and Autoimmune Disease", *Current Topics in Microbiology and Immunology*, vol. 167, Springer–Verlag, Berlin, 1991, pp. 161–189.

D. L. Wilkinson et al., "Evidence for a functional subclass of the RTLV–H family of human endogenous retrovirus–like sequences", *J. Virol.*, vol. 67, pp. 2981–2989, (1993).

Wollinsky et al., "Liquorpherese bei 10 Patienten mit Multipler Sklerose [Fluid Phoresis in 10 Patients With Multiple Sclerosis]", *Verhandlungen der Deutschen Gesellschaft fur Neurologie*, vol. 7, 1992, pp. 444–445.

Woodland, et al., "An Endogenous Retrovirus Mediating Deletion of αβ T cells?", *Nature*, vol. 349, Feb. 7, 1991, pp. 529–530.

PROCESS FOR THE PRODUCTION OF A VIABLE CELL CULTURE INFECTED BY A MULTIPLE SCLEROSIS-ASSOCIATED VIRUS

This is a Division of application Ser. No. 08/157,060 filed Feb. 2, 1994, now U.S. Pat. No. 5,585,262, which is a division of the national stage of International application Ser. No. PCT/FR93/00337, filed Apr. 2, 1993.

BACKGROUND OF THE INVENTION

The present invention relates to the production and maintenance of a viable cell culture or line infected by the virus associated with multiple sclerosis (MS). Such a culture in fact has the advantage of constituting a biological material which expresses the activity of the virus associated with MS, and as a result can be used for various experimental aims, in particular for tests for identification and characterization of the virus, but also for clinical or therapeutic aims.

"Viable culture" is understood as meaning any culture which keeps infected cells alive such that the virus associated with MS is expressed and which preserves the mitotic potency of said cells, in particular during culture of the latter by successive passages.

The present invention relates to a process for in vitro culture of cells infected by a virus present in individuals suffering from multiple sclerosis and to the infected cell lines thus obtained.

DESCRIPTION OF THE PRIOR ART

Multiple sclerosis (MS) is a demyelinizing disease of the central nervous system (CNS) which has been suspected for several years of being associated with a virus, although the causal agent has still not been determined with certainty.

Several works have supported this hypothesis of a viral etiology of the disease, but none of the known viruses tested have proven to be the causal agent sought.

Consequently, the observation in patients suffering from multiple sclerosis of phenomena comparable to an autoimmunity reaction has led to an "essential" auto-immune etiological hypothesis (Lisak R. P., Zweiman B. New Engl. J. Med. 1977; 297, 850–853, and Lassmann H. and Wisniewski H. M. Arch. Neurol. 1979; 36, 490–497). However, this autoimmunity directed against certain components of the central nervous system has proven to be not very specific to MS and frequent in inflammations of the CNS which may or may not be associated with an infection, as has been demonstrated by Hirayama M. et al. (Neurology 1986; 36, 276–8) Kenneth G. Warren et al. (Annals of Neurology 1986; 20, 20–25), Suzumura A. et al. (Journal of Neuroimmunology 1986; 11, 137–47) and Tourtelotte W. et al. (Journal of Neurochemistry 1986; 46, 1086–93). Moreover, as E. J. Field noted (The Lancet 1989; 1, 1272), none of the immunosuppressive therapeutic agents has achieved decisive results against MS.

One hypothesis has been put forward, according to which a retrovirus is said to be the cause of the disease. The discovery by A. Gessain et al. (J. Infect. Disease 1988; 1226–1234) of neurological syndromes associated with the HTLV-1 virus, known at the start as the agent of T-cell leukemia in adults, has led several authors such as H. Koprowski et al. (Nature 1985; 315, 154), M. Ohta et al. (J. Immunol. 1986; 137, 3440), E. P. Reddy et al. (Science 1989; 243, 529), S. J. Greenberg et al. (Proc. Natl. Acad. Sci. USA 1989; 86, 2878), J. H. Richardson et al. (Science 1989; 246, 821), S. L. Hauser et al. (Nature 1986; 322, 176) and A. Karpas et al. (Nature 1986; 322, 177) to investigate an involvement of this human retrovirus in MS, although without success or with results which suggest cross-reactions.

There is moreover an animal model which is very close to MS and is induced by a retrovirus: the MAEDI-VISNA virus in sheep. It is known that natural infection by this virus causes an ovine disease close to MS, as reported by Johnson R. T. (Rev. Infect. Dis. 1985; 7, 66–67), Narayan O. and Cork L. C. (Rev. Infect. Dis. 1985; 7, 75–82). Experimental infection of sheep by intra-ventricular inoculation of neurovirulent strains of the VISNA virus has established the responsibility of this virus in the origin of this demyelinizing infection in sheep. As explained by Nathanson N. et al. (Rev. Infect. Dis. 1985; 7, 75–82), Hoffman P. M. and Panitch H. S. ("Handbook of Clinical Neurology, 12; Viral diseases" R. R. McKendall, ed., Elsevier Science Publishing, Amsterdam, 1989, 453–466) and A. Haase (Nature 1986; 322, 130–136), it differs a little from the natural infection, but nevertheless remains close to MS. It is furthermore interesting to note that in all the works carried out on this subject by the abovementioned authors, the Visna virus is found in the cells of the plexus choroideus in the brain of infected sheep, which constitute a site of dormancy and of occasional replication of the Visna pro-virus; the location of these cells at the cephalorrachidian blood/fluid boundary certainly explains this phenomenon.

All these results suggest a role of an unknown retrovirus in MS.

Works by H. PERRON et al. (Res. Virol. 1989; 140, 551–561 in "Current concepts in multiple sclerosis" Wieth ölter et al., editors Amsterdam, Elsevier, 1991, pages 111–116 and The Lancet 1991; 337, 862–863) have recently allowed a non-lymphoid cell line to be isolated from a lumbar puncture of the cephalorrachidian fluid of a patient suffering from MS, and demonstration of the presence of a virus having the characteristics of a retrovirus and showing in particular an reverse transcriptase activity in the supernatant of cell cultures of this line. Examination of the cells of this line by electron microscopy has demonstrated viral particles having a diameter of between about 110 and 140 nm, the size of the particles varying according to whether the particles are mature or immature. Furthermore, a serological study by the ELISA technique using a cell extract from infected cells of this line showed, with 40 sera of patients of whom 20 are suffering from MS (certain MS) and 20 are presumed patients (probable MS), 60% of positive results. A comparative study with 40 sera of patients suffering from neurological diseases other than MS gave only 5% of positive results. This line, which the authors have called LM7, is clonal and non-immortal, and immunocytochemical and ultrastructural study of this line have characterized its leptomeningeal origin.

However, this virus has proven very difficult to study because on the one hand it expresses itself very weakly in vitro in the primary cell line of leptomeningeal origin, and on the other hand this cell line degenerates quite rapidly after about 30 passages by extinction of its mitotic potency such that it no longer allows viral expression.

In addition, the authors have proposed a new approach (H. Perron et al., The Lancet, volume 337, 862–863, (1991)) which comprises taking a blood sample from a patient suffering from MS, culturing monocytes and collecting the supernatant to verify expression of an reverse transcriptase activity, either directly in the ultracentrifugation residue or after sedimentation at equilibrium over a sucrose gradient. It has thus been demonstrated that there is a peak of reverse transcriptase activity in the supernatant in patients suffering from MS and that this activity is found in the fraction having a density of about 1.17 g/ml. Examination of the infected cells by electron microscopy has demonstrated particles similar to retroviruses of 100 to 120 nm, which are found in the ultracentrifugation residues of supernatants from cultures which express an increased reverse transcriptase activity. However, as explained by the authors, a cytopathic effect was observed in the infected funicular blood cells but is no longer detectable, so that this culture method is not satisfactory for an in-depth study of the characteristics of this virus. The centrifugation residues containing cell debris and potentially viral particles were then cultured on funicular blood cells to demonstrate a viral expression.

It is thus essential to have available a process for in vitro culture of cells infected by a virus associated with multiple sclerosis, such a process not being available to date.

SUMMARY OF THE INVENTION

The inventors have first put forward and verified the hypothesis that human plexus choroideus cells could be cells which are permissive to the virus found in patients suffering from MS. On the basis of this discovery of the properties of human plexus choroideus cells, the present inventors have developed a process for in vitro culture of cells infected by a virus associated with MS and have demonstrated that said process allows production of infected cell lines which ensure good replication and expression of the virus.

The process according to the invention comprises:
- cultivation of human cells infected by a viral strain associated with MS to obtain at least one culture of primary cells infected by said viral strain,
- cultivation of permissive human cells, preferably non-infected human plexus choroideus cells, which are capable of becoming infected with a replicating said viral strain to obtain at least one permissive culture,
- cocultivation of at least one sample of a culture of infected primary cells and a sample of a permissive culture to obtain a first derived culture infected by a said viral strain,
- cultivation in series, that is to say by successive subcultures, of the first infected derived culture; for this purpose, the stage comprising cocultivation, for example for 5 to 8 days, of a new sample of a non-infected permissive culture and a sample of the first infected derived culture, or of a subculture of the latter, is repeated in the course of time to obtain a new subculture of the same first infected derived culture constituting a viable viral culture.

In addition, according to the invention, the process first comprises culture of human plexus choroideus cells in a suitable culture medium comprising at least amino acids, vitamin factors, inorganic salts and glucose in total weight concentrations of between, respectively, 400 and 2250 mg/l, 3.5 and 130 mg/l, 9100 and 13,000 mg/l and 1000 and 6000 mg/l; then bringing into contact the said plexus choroideus cells cultured in this way, in their culture medium, with primary cells infected by the virus or a culture supernatant containing the virus, or with cells derived from the said infected cells, under given conditions which allow propagation of the virus of the infected cells to the cultured cells, its replication and its expression.

A particularly suitable culture medium for the process described above comprises:

between 400 and 2250 mg/l of amino acids
between 3.5 and 130 mg/l of vitamins
between 9100 and 13,000 mg/l of inorganic salts
between 1000 and 6000 mg/l of glucose
and, if appropriate, at least one growth factor chosen from ECGF and basic FGF.

More particularly, and by way of a non-limitative example, the culture or coculture medium comprises the following constituents:

one or more amino acids chosen from the following compounds, viz.:
- arginine: 100 to 500 mg/l, preferably 100 to 300 mg/l
- cysteine and/or cystine: 25 to 300 mg/l, preferably cystine: 25 to 100 mg/l
- glutamine: 200 to 1000 mg/l, preferably 200 to 500 mg/l
- histidine: 5 to 50 mg/l, preferably 5 to 20 mg/l
- isoleucine: 20 to 100 mg/l, preferably 20 to 60 mg/l
- leucine: 20 to 100 mg/l, preferably 20 to 60 mg/l
- lysine: 20 to 100 mg/l, preferably 20 to 80 mg/l
- methionine: 5 to 50 mg/l, preferably 5 to 30 mg/l
- phenylalanine: 10 to 70 mg/l, preferably 10 to 50 mg/l
- threanine: 15 to 100 mg/l, preferably 15 to 60 mg/l
- tryptophan: 2 to 30 mg/l, preferably 2 to 25 mg/l
- tyrosine: 10 to 70 mg/l, preferably 10 to 50 mg/l
- valine: 10 to 80 mg/l, preferably 10 to 60 mg/l one or more vitamins chosen from the following compounds:
- pantothenate: 0.15 to 5 mg/l, preferably the calcium salt: 0.15 to 2 mg/l
- choline: 0.5 to 10 mg/l, preferably the chloride salt: 0.5 to 5 mg/l
- folic acid: 0.5 to 10 mg/l, preferably 0.5 to 5 mg/l
- inositol: 1 to 70 mg/l, preferably 1 to 50 mg/l
- nicotinamide and/or niacinamide: 0.5 to 10 mg/l, preferably nicotinamide: 0.5 to 5 mg/l
- pyridoxine and/or pyridoxal: 0.5 to 10 mg/l, preferably pyridozine HCl: 0.5 to 5 mg/l
- riboflavin: 0.05 to 1 mg/l, preferably 0.05 to 0.5 mg/l
- thiamine: 0.5 to 10 mg/l, preferably 0.5 to 5 mg/l one or more inorganic salts chosen from the following compounds, viz.:
- calcium salts: 100 to 200 mg/l, preferably anhydrous $CaCl_2$
- potassium chloride: 350 to 450 mg/l
- magnesium salts: 40 to 60 mg/l, preferably anhydrous $MgSO_4$
- sodium chloride: 6000 to 8000 mg/l
- $HCO_3$ salts: 2000 to 3000 mg/l, preferably $NaHCO_3$
- $HPO_4$ salts: 600 to 1000 mg/l, preferably anhydrous $Na_2HPO_4$
- and glucose: 1000 to 6000 mg/l, preferably D-glucose.

The amino acids are advantageously chosen from those of the natural L series.

The medium may also comprise at least one antibiotic, preferably a mixture of penicillin and streptomycin, and, if desired, clindamycin, to prevent mycoplasmic contamination.

According to one embodiment of the invention, the medium furthermore comprises at least one growth factor chosen from ECGF ("endothelial cell growth factor"), also called acid FGF, and basic FGF ("fibroblast growth factor"), in varying proportions which the expert can determine with the aid of his general knowledge of cell cultures and products available to him. By way of example, the concentrations of growth factor is between 1 and 50 μg per liter of culture medium, or between 50 and 150 μg/l in the presence of heparin. The growth factor chosen is advantageously ECGF in a concentration of 10 μg/l, in the presence of heparin as previously.

In a particular embodiment of the invention, the permissive human plexus choroideus cells before culture are non-infected cells.

According to a particular embodiment of the invention, the culture of primary infected cells, the first infected derived culture or any subculture of the latter, before being brought into contact with the permissive cells cultured, are first treated by irradiation, for example by irradiation with X-rays.

According to a preferred embodiment of the invention, several cultures of primary cells infected by viral strains or isolates of MS which differ respectively are obtained, and the first coculture is carried out by coculture of a sample of the permissive culture and of several samples of cultures of primary cells or of subcultures which differ respectively. A mixture of viral strains is thus obtained in the viable cell culture, allowing inter-strain recombination, possible complementing of defective genomes and the emergence of recombinant strains, the suitability of which for certain criteria may be greatly increased. This also allows strains which are highly suitable for culture in vitro to be obtained, or for replicative strains to be obtained from defective strains.

The term "infected cells" as used in the present invention refers:

i) to primary infected cells obtained from a culture of cells produced directly from a sample of tissue or biological fluid in vivo or post mortem from an infected individual, and to derived cells obtained by successive passages of these primary cells, and ii) to secondary infected cells obtained by coculture of primary infected cells and permissive cells, and to derived cells obtained by passages of these secondary cells.

"Primary cells" is understood as meaning cells or cultures originating directly from a sample of tissue or of biological fluid and passed in culture without any coculture or any inoculation of viral strains produced from other cells, inasmuch as these so-called primary cells do not show a potential for abnormal proliferation (immortalization or transformation).

The infected cells sampled in vivo or post mortem can be any cells infected by the virus, for example leptomeningeal cells isolated from the cephalorrachidian fluid of a patient (H. Perron et al., Res. Biol., 140, 551–561 (1989)), myeloid cells found in the blood, in the cephalorrachidian fluid, in the tissues or in the bone marrow, in particular macrophages or monocytes (H. Perron et al., The Lancet, volume 337, 862–863, Apr. 6, 1991), and in particular lymphocytes (S. A. Haahr et al., The Lancet, volume 337, 863–864, Apr. 6, 1991) or analogous cells.

The term "macrophage(s)" refers to cells which are derived directly from blood monocytes, to cells which reside in tissues (microgliocytes, Kupffer cells) and cells of the reticulo-endothelial system, in particular Langerhans cells.

The permissive cells are cells which can become infected and allow replication of a given virus, with production of extra-cellular viral particles which can be studied, in particular for their reverse transcriptase activity in the supernatants.

The term "passage" refers to a cell culture in series and corresponds to the dissociation of cells from one culture bottle for transfer into one or more new bottles.

It is well known to experts that spontaneous or induced modifications may survive in the karyotype during storage or passages. Cells derived from a reference cell line thus may not be exactly identical to the original cultures or cells. Furthermore, the genetic variability or retroviruses is well known, and a given retroviral strain may modify its characteristics by spontaneous or induced mutations in the course of cultures.

The invention will be better understood by reading the detailed description which is to follow, with reference to the attached figures, in which.

EXAMPLE 1

In vitro preparation of a culture of primary cells infected by a virus present in a patient suffering from MS.

The methods for preparation of primary cultures starting from primary infected cells, for example leptomeningeal cells, monocytes or lymphocytes, and the conditions for their growth in vitro are known to the expert (see the references above). Another candidate for preparation of a culture of primary infected cells is represented by the plexus choroideus cells. The plexus choroideus cells are cultured in accordance with the conventional techniques, after explanation of human plexus choroideus obtained post mortem. The anatomical piece sampled under sterile conditions is dilacerated delicately with tweezers and placed in a trypsin solution for a few minutes at about 37° C. The tissue fragments are collected after centrifugation at a low speed (500 revolutions per minute) and the supernatant is recentrifuged at 1600 revolutions per minute for 5 to 10 minutes. The residue is taken up in the culture media and the mixtures are placed in a flask where only the adhering cells will remain after the medium has been changed.

EXAMPLE 2

Preparation of a culture of cells permissive to a virus present in patients suffering from MS.

Culture of Plexus Choroideus Cells

Non-infected plexus choroideus cells obtained after explantation post mortem of the human plexus choroideus are cultivated in an RPMI 1640 medium (marketed by Boehringer Mannheim) comprising: penicillin (200,000 U/l), streptomycin (200 mg/l), clindamycin (75 mg/l), L-glutamine (6 mM/l), 1% of pyruvate, serum, preferably 20 to 30% of fetal calf serum decomplemented by incubation at 56° C. for 30 minutes, and 1% of non-essential amino acids (Boehringer Mannheim MEM. A.A.N.E. 100× ref: 210293). The culture medium advantageously moreover comprises a growth factor, such as endothelial cell growth factor (ECGF), combined with heparin (BOEHRINGER ref. 1/79/87: ECGF about 1 to 20 ng/ml comprising 50–150 μg/ml of heparin).

EXAMPLE 3

Coculture of a primary cell line infected by a virus present in a patient suffering from MS and cells permissive to the virus.

Cells of a culture of primary cells infected, as described in Example 1, by a virus present in an individual suffering from MS, for example the LM7 virus, identified in the preamble of the present description, are dissociated from their culture flask, the viable cells adhering to the base of the flask, and are taken up in a culture medium suitable for coculture, that is to say in the culture medium of the plexus choroideus cells, according to Example 2. In parallel, the non-infected plexus choroideus cells are dissociated from their culture medium described in Example 2 in a solution of trypsin-EDTA. The cells are then centrifuged and resuspended in their culture medium, and are added to the infected cell culture flask. The flask is placed in an oven under $CO_2$ and the plexus choroideus cells are allowed to adhere to and proliferate on the base of the flask, which already contains infected cells, for 24 hours. The medium is changed after 24 hours and the mixture of adhering cells is left in the oven under $CO_2$ until the cell proliferation produces a confluent layer, that is to say a carpet of adhering cells. At this stage, the cells are maintained for a further 5 to 7 days to ensure transfer of the virus from the infected cells to the plexus choroideus cells. The cell culture is then divided into two and passed into two new flasks, each of which is seeded with dissociated suspended plexus choroideus cells. These new cultures are subjected to the same conditions as described above for adhesion and proliferation of the cells and transfer, expression and replication of the virus. The cell cultures are then regularly divided into two and subjected to passages for as long as the mitotic potential of the permissive cells allows. These cells, which harbor and produce a virus of the LM7 type, can in their turn be used to infect new cells by coculture as described above, and thus to maintain the viral strain in culture.

The culture media are always changed at least twice a week and always on the day following a new passage, that is to say at each new seeding of a flask with dissociated suspended cells.

Prior to the coculture, the cells which harbor a viral strain can be irradiated, if appropriate, in a manner such that their subsequent proliferation within a newly infected culture is avoided. The irradiation can be realized, for example, with a total dose of 6000 rad of X-rays.

Monitoring of the transmission of a virus of the LM7 type and of the maintenance of its expression in the cells obtained after coculture with cells which produce such a virus is carried out by analysis of the reverse transcriptase activity in the supernatant of the cultures, which is removed regularly to renew the medium.

The analysis of the activity of this characteristic enzyme of retroviruses is carried out under conditions determined by the LM7 strain. In the case of the LM7 virus, the reaction conditions are those described by H. Perron et al. (Res. Virol. 1989; 840, 551–561).

The culture supernatants, having a minimum volume of 15 ml, are collected twice a week, precentrifuged at 10,000 revolutions per minute for 30 minutes to remove the cell debris and then ultracentrifuged at 35,000 revolutions per minute for 2 hours to sediment the retroviral particles. The residues are removed (final volume concentrated about 1000 times in a 0.05 M Tris/HCl buffer, pH 8 to 9.5) and stored at −80° C. for subsequent analysis of the reverse transcriptase activity.

EXAMPLE 4

Analysis of the reverse transcriptase activity for monitoring production of viral particles of the LM7 type in the supernatant of newly infected plexus choroideus cells.

All the stages are carried out with sterile equipment and solutions in order to avoid any interference with bacterial nucleases or proteases, in particular during the incubation phases at 37° C.

The residues containing the concentrated viral particles are thawed and homogenized: 20 µl samples are taken and added to a reaction mixture comprising: 5 µl of 0.5 M Tris-0.04 M DTT, pH 8.2/5 µl of 0.1 MNaCl/5 µl of 0.3 M $MgCl_2$/23 µl of doubly distilled $H_2O$/10 µl of 2% NP40/2 µl of polyCm-oligodG12–18 (10 U O.D./ml; Pharmacia)/5 µl of 3H-, 3H-guanosine triphosphate (1 mCi/ml); NEN). The glass tubes containing the mixtures are incubated at 37° C. for 75 minutes. The reaction is stopped by adding 75 µl of a solution, at +4° C., comprising: 12.5% of $H_2O$ saturated with sodium phosphate, 12.5% of $H_2O$ saturated with sodium pyrophosphate and 20% of trichloroacetic acid (TCA). After 30 minutes to 1 hour at 4° C., the tubes are filled with a solution of 5% of TCA, emptied and rinsed 5 times with the 5% strength solution of TCA onto a cellulose acetate membrane (Sartorius ref. 11106 25 N; pore diameter; 0.45µ; membrane diameter: 25 mm), through which the samples are filtered into a 1125 fraction collector (Millipore; ref. XX2702550). Before being removed, the membranes are rinsed once more with 20 ml of 5% strength TCA. The membranes are then placed in small flasks which are filled with scintillating liquid (Ready-Safe, Beckman) and the activity is measured in a beta counter, in cpm (counts per minute) and dpm (disintegrations per minute).

Each sample is tested in triplicate and the mean of the values is used as the result. If the difference between this mean and one of the measurements exceeds twice the standard deviation measured on the reference values, the corresponding sample is tested again.

Figure 1:
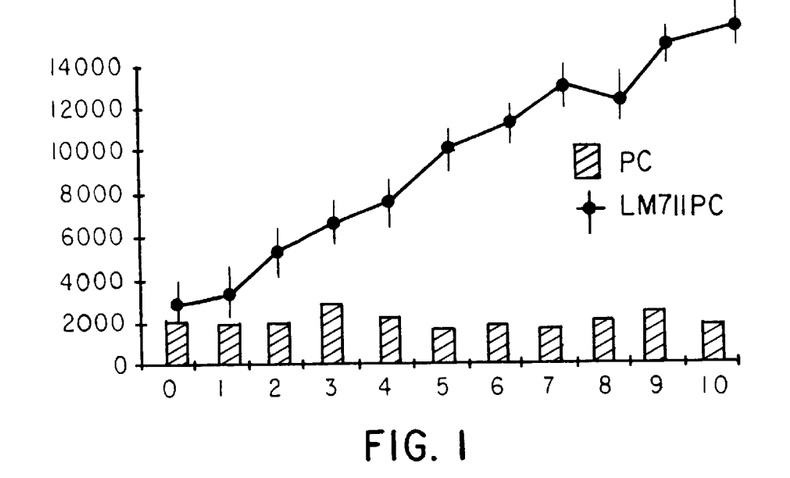
FIG. 1 represents the kinetics of the reverse transcriptase activity in disintegrations per minute for $10^4$ cells as a function of the number of passages, determined in the supernatant of a culture of human plexus choroideus cells of reference LM 711 PC infected by coculture with leptomeningeal cells themselves infected by the virus LM7, and a comparison with the reverse transcriptase activity determined in non-infected human plexus choroideus cells which were sampled post mortem from a patient and have not been cocultivated.

It was thus possible to plot the kinetics of the production of virions sorted out in the supernatant of newly infected human plexus choroideus cell cultures after coculture with leptomeningeal cells infected by the LM7 virus (FIG. 1).

Figure 2:
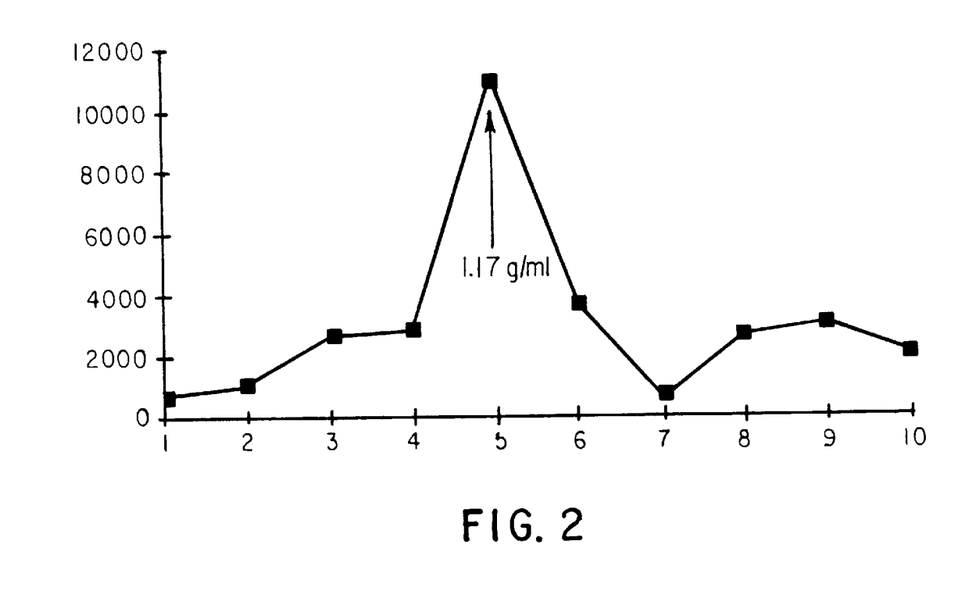
FIG. 2 represents the reverse transcriptase activity of particles which sediment at a known density for the retroviruses; the number of disintegrations per minute, tested on 20 μl samples in each fraction, is plotted on the ordinate and the fraction is plotted by its number on the abscissa.

To verify that the reverse transcriptase activity is certainly associated with particles of the retroviral type, the virion residues concentrated by ultracentrifugation of supernatants of the culture on a cushion of glycerol are placed on sucrose gradients (15 to 50% weight/weight) and ultracentrifuged at +4° C. for 16 hours at 100,000 g in a cup rotor. 10 fractions are collected and 20 µl samples of each fraction are taken for analysis of the reverse transcriptase activity as described above. The specific activity peak is found in the fraction having a density of about 1.17 g/ml (refractometric analysis), which corresponds to an equilibrium sedimentation density known for retroviral particles (1.16 to 1.18 g/ml). An example of this analysis over a gradient is shown in FIG. 2.

The present invention also relates to any culture or cell line infected by a human viral strain associated with multiple sclerosis, comprising:

either strain cells sampled on or belonging to a viable infected cell culture obtained by a process as described above, or derived cells obtained by modifying the genome of the said strain cells, but without altering their phenotype of cells infected by a virus of multiple sclerosis.

We claim:

1. A process for producing a viable infected culture or cell line comprising cells infected by at least one human viral strain associated with multiple sclerosis (MS) having reverse transcriptase activity, said process comprising:

(a) cultivating cells infected by said viral strain to obtain at least one culture or cell line of primary cells infected by said viral strain, (b) cultivating non-infected leptomeningeal or plexus choroideus cells that are permissive to said viral strain to obtain at least one non-infected permissive culture, (c) cocultivating at least one sample of said culture or cell line of primary infected cells and at least one sample of said at least one non-infected permissive culture to obtain a first derived culture of leptomeningeal or plexus choroideus cells infected by said viral strain, and (d) cultivating the first infected derived culture in series, by cocultivating a new sample of the at least one non-infected permissive culture and a sample of the first infected derived culture, or of a subculture of the first infected derived culture, to obtain a new subculture of the first infected derived culture, constituting a viable viral culture or cell line.

2. The process as claimed in claim 1, wherein the culture or cell-line of infected primary cells is obtained from cells infected by said viral strain, said cells being selected from the group consisting leptomeningeal cells, plexus choroideus cells, myeloid blood cells and lymphocytes.

3. The process as claimed in claim 1, wherein the permissive culture is obtained from human plexus choroideus cells.

4. The process as claimed in claim 1, wherein several of said primary cultures infected by differing viral strains are obtained in step (a), and wherein step (c) is carried out by cocultivating a sample of the permissive culture and several differing samples of said infected primary cultures.

5. The process as claimed in claim 1, further comprising providing a culture medium for cultivating said permissive cells, wherein said culture medium comprises:

between 400 and 2250 mg/l of amino acids;

between 3.5 and 130 mg/l of vitamins;

between 9100 and 13,000 mg/l of inorganic salts; and between 1000 and 6000 mg/l of glucose.

6. A viable cell culture infected by a human viral strain associated with multiple sclerosis, which comprises viable cells sampled from or belonging to a viable infected culture or cell line obtained by a process as claimed in claim 1, or viable derived cells obtained by modifying the genome of said cells, without altering their phenotype.

7. The process as claimed in claim 1, wherein the culture of infected primary cells is obtained from cells infected by said viral strain and selected from the group consisting of macrophages and monocytes.

8. The process as claimed in claim 5, wherein said culture medium further comprises at least one growth factor selected from the group consisting of endothelial cell growth factor and basic fibroblast growth factor.

9. The process as claimed in claim 1, wherein said at least one culture or cell line is an LM7-type culture or cell line.

10. A process for producing a viable infected culture or cell line comprising cells infected by at least one human viral strain associated with multiple sclerosis (MS) having reverse transcriptase activity, said process comprising:

(a) cultivating cells infected by said viral strain and selected from the group consisting of leptomeningeal cells, plexus choroideus cells, myeloid blood cells and lymphocytes, to obtain at least one culture or cell line of primary cells infected by said viral strain, (b) cultivating plexus choroideus cells that are permissive to said viral strain to obtain at least one non-infected permissive culture, (c) cocultivating at least one sample of said culture or cell line of primary infected cells and at least one sample of said at least one non-infected permissive culture to obtain a first derived culture of plexus choroideus cells infected by said viral strain, and (d) cultivating the first infected derived culture in series, by cocultivating a new sample of the at least one non-infected permissive culture and a sample of the first infected derived culture or of a subculture of the first infected derived culture to obtain a new subculture of the first infected derived culture, constituting a viable viral culture or cell line.

11. The process as claimed in claim 10, wherein said human cells are LM7-type cells.

12. A process for producing a viable infected culture or cell line comprising cells infected by multiple sclerosis (MS), said process comprising:

(a) cultivating cells infected with MS to obtain at least one culture or cell line of primary infected cells, (b) cultivating non-infected leptomeningeal or plexus choroideus cells that are permissive to MS to obtain at least one non-infected permissive culture, (c) cocultivating at least one sample of said culture or cell line of primary infected cells and at least one sample of said at least one non-infected permissive culture to obtain a first infected derived culture, and (d) cultivating the first infected derived culture in series, by cocultivating a new sample of the at least one non-infected permissive culture and a sample of the first infected derived culture or of a subculture of the first infected derived culture to obtain a new subculture of the first infected derived culture, constituting a viable culture or cell line.

13. The process as claimed in claim 1, wherein said infected and non-infected cells are nervous system cells.

14. The process as claimed in claim 1, wherein the permissive culture is obtained from plexus choroideus cells.

15. The process as claimed in claim 1, wherein the infected and non-infected cells are human cells.

16. The process as claimed in claim 10, wherein the infected and non-infected cells are human cells.

* * * * *